United States Patent [19]

Igarashi et al.

[11] Patent Number: 5,518,904
[45] Date of Patent: May 21, 1996

[54] METHOD OF PRODUCING ALPHA CRYSTALS OF L-PHENYLALANINE

[75] Inventors: Koji Igarashi; Mitsuhiro Kishino; Mitsuyoshi Seki; Tomoharu Takenouchi; Takahiko Kureyama, all of Kawasaki, Japan

[73] Assignee: Ajinomoto Co., Inc., Tokyo, Japan

[21] Appl. No.: 11,751

[22] Filed: Feb. 1, 1993

[30] Foreign Application Priority Data

Jan. 30, 1992 [JP] Japan .................................. 4-015137

[51] Int. Cl.$^6$ ...................................................... C12P 13/22
[52] U.S. Cl. ........................................................ 435/108
[58] Field of Search ............................ 435/108; 562/443, 562/445

[56] References Cited

U.S. PATENT DOCUMENTS 5,118,840  6/1992  Kano ......................................... 562/443

FOREIGN PATENT DOCUMENTS 0049250  5/1975  Japan .
0049249  5/1975  Japan .
62-288   3/1987  Japan .

OTHER PUBLICATIONS

Perry's Chemical Engineers' Handbook, pp. 19–24 to 19–40, Publishers: McGraw–Hill, Inc., 1984.

Kirk–Othmer Encyclopedia of Chemical Technology, vol. 7, Publishers: John Wiley & Sons, Inc., pp. 243–285, 1979.

Primary Examiner—Marian C. Knode
Assistant Examiner—S. Saucier
Attorney, Agent, or Firm—Oblon, Spivak, McClelland, Maier, & Neustadt

[57] ABSTRACT

A method of producing L-phenylalanine employing a microorganism in which cultivation of the microorganism is continued while precipitating alpha-crystals of L-phenylalanine in the culture by means of seed crystals or a pH shift.

9 Claims, No Drawings

METHOD OF PRODUCING ALPHA CRYSTALS OF L-PHENYLALANINE

FIELD OF THE INVENTION

The present invention relates to a method of producing L-phenylalanine (hereinafter referred to as "Phe") employing a microorganism. Phe is widely used as a raw material for medicines, sweeteners and chemical products.

DISCUSSION OF THE BACKGROUND

Conventional methods which employ a microorganism to produce Phe involve culturing the microorganism in a liquid nutrient medium or incubating it with a raw material substance in a reaction liquid to produce and accumulate Phe in the culture or in the reaction liquid and the Phe is then harvested.

The crystal morphology of Phe is known to include alpha-crystals (hereinafter referred to as Phe-alpha-crystals) and beta-crystals (monohydrate crystals—hereinafter referred to as Phe-beta-crystals). Regarding the shape of the crystals, Phe-alpha-crystals are tabular or flaky, while Phe-beta-crystals are extremely fine, needle-like crystals. In conventional production of Phe employing a microorganism, the crystals which precipitate out of the culture medium due to accumulation of Phe to a concentration higher than its supersaturated solubility in the medium are always Phe-beta-crystals if no measures are taken to control the crystal form. Precipitation of Phe-beta-crystals during cultivation causes the viscosity of the culture medium to increase and over-foaming of the culture which makes continuation of the cultivation difficult. If further continuation of the cultivation were attempted under these conditions, it would cause another problem, that of scattering of the culture medium out of the cultivation device and, as a result, the production of Phe would be substantially impossible thereafter. Therefore, a microorganism which does not produce and accumulate Phe in an amount which saturates the culture medium must be employed, or, when microorganisms having a high producing ability are cultured, control of the amount of the raw material supplied or control of the amount of the culture medium must be effected to limit the amount of Phe accumulated to an amount lower than the solubility thereof. For these reasons, the productivity of Phe by conventional methods is low. Therefore, development of a drastically improved method for reducing the cost of producing Phe by employing microorganisms has been desired.

SUMMARY OF THE INVENTION

An object of the present invention is to provide a more inexpensive and more efficient method of producing Phe employing a microorganism by seeding the culture medium with alpha-crystals of Phe or by adjusting the pH of the culture medium to a range from 7.8 to 8.3 once the culture medium approaches the saturation concentration of Phe.

DETAILED DESCRIPTION OF THE PREFERRED EMBODIMENTS

The present inventors earnestly made repeated studies for the purpose of developing a less expensive and more efficient method of producing Phe employing a microorganism and, as a result, have found that cultivating a microorganism having the ability to produce Phe while precipitating Phe-alpha-crystals in the culture medium brings about smooth and successive cultivation of Phe even after it accumulates to an amount more than the solubility of Phe in the culture. Efficient production of Phe is possible in this way. Specifically, the present invention provides a method of producing Phe in which cultivation of the Phe-producing microorganism is conducted while precipitating Phe-alpha-crystals in the culture.

The microorganism to be used in the present invention can be a strain belonging to the genus Brevibacterium, Corynebacterium, Bacillus, Escherichia, or the like, and having the ability to produce Phe. Specific examples of such microorganisms include the following strains which have been deposited with the National Institute of Bioscience and Human-Technology, Fermentation Research Institute, Agency of Industrial Science and Technology, Ministry International Trade and Industry, 1–3, Higashi 1-chome, Tsukuba-shi, Ibaraki-ken 305, Japan Brevibacterium lactofermentum AJ12637 (FERM BP-4160; Japanese Patent Application No. 3-211052)

Bacillus subtilis AJ12097 (FERM BP-609, Japanese Patent Publication No. 3-47820)

For producing Phe in accordance with the method of the present invention using such a microorganism, cultivation is effected in a liquid medium containing carbon sources, nitrogen sources, inorganic salts and optionally other organic minor nutrients and nutritious substances needed by the microorganism to be cultured therein. Suitable carbon sources are saccharides, such as glucose, sucrose, molasses and hydrolysates of starch; organic acids such as acetic acid and propionic acid; and alcohols such as ethanol and propanol. Examples of nitrogen sources are ammonium sulfate, ammonium nitrate, ammonium chloride, urea and ammonia. Suitable organic minor nutrients are, for example, amino acids, vitamins, fatty acids, nucleic acids, as well as yeast extracts, peptone, Casamino acid and hydrolysates of soybean protein containing them. In addition, Phe precursors such as phenylpyruvic acid and cinnamic acid are also usable as raw materials in the medium. The carbon sources, nitrogen sources and other raw materials constituting the medium may all be added to the original medium prior to initiation of cultivation, or they may be continuously or intermittently added to the medium during the course of cultivation.

The temperature for cultivation may be from 10° to 50° C., preferably from 30° to 40° C.; and the pH value of the medium may be from 4.0 to 9.0, preferably from 5.5 to 8.0. For adjustment of the pH value, inorganic or organic acidic or alkaline substances as well as urea, calcium carbonate and ammonia gas are usable.

The most important technique in carrying out the present invention is to artificially precipitate Phe-alpha-crystals in the presence of a supersaturated concentration of Phe in the culture. In other words, Phe-alpha-crystals are precipitated after the concentration of Phe reaches its solubility and before the crystals spontaneously precipitate out. Because Phe-alpha-crystals are much more unstable than Phe-beta-crystals when the concentration of dissolved Phe becomes higher than its solubility, Phe-beta-crystals spontaneously begin to precipitate out of the culture unless specific means are applied to the culture system to prevent it, whereby continuation of the cultivation becomes difficult thereafter.

Means of precipitating Phe-alpha-crystals in the culture at the point when the accumulated concentration of Phe has reached a supersaturated state include a method of adding seed crystals of Phe-alpha-crystals to the culture and a method of varying the pH value of the culture.

Where Phe-alpha-crystals are precipitated out by the method of adding seed crystals of Phe-alpha-crystals to the culture, the time of adding the seed crystals is preferably at the point just when the concentration of Phe has exceeded its solubility in the culture after initiation of cultivation. However, even if the seed crystals are added to the culture medium before the Phe concentration reaches saturation they dissolve in the culture and further addition of seed crystals under a supersaturated condition assists precipitation of alpha-crystals of Phe dissolved in the culture. In general, the presence of Phe crystals at approximately 1% of the quantity of dissolved Phe in the culture medium brings about precipitation of Phe-alpha-crystals from Phe produced thereafter in the culture. Therefore, the amount of Phe-alpha-crystals to be added is not specifically defined but may be selected freely. Where the concentration of the accumulated Phe has reached its solubility, the crystals are added to the culture, generally in an amount of from 1 to 5% of the quantity of dissolved Phe. Seed Phe-alpha-crystals may be added to the culture as they are, or they may be added in the form of a slurry prepared by suspending them in a suitable amount of water.

Where Phe-alpha-crystals are precipitated out by the method of varying the pH value of the culture, the pH value may be shifted to a range of from 7.8 to 8.3 from the vicinity of pH 7.0, which is used for general Phe fermentation, at the point when the concentration of the accumulated Phe has exceeded its solubility after initiation of cultivation. The pH change may be effected by addition of an alkaline substance such as ammonia gas or potassium hydroxide.

Continuation of cultivation after Phe-alpha-crystals have thus precipitated out in the culture gives further precipitation of the Phe produced thereafter in the form of alpha-crystals without increasing the viscosity of the culture or causing over-foaming of it, and therefore the culture process may be effected smoothly.

After finishing the cultivation, the obtained culture is concentrated and crystallized, the crystals are separated and subjected to repeated dissolution and crystallization to obtain the intended Phe crystals of high purity with ease.

Other features of the invention will become apparent in the course of the following descriptions of exemplary embodiments which are given for illustration of the invention and are not intended to be limiting thereof.

EXAMPLE 1

Cells of *Brevibacterium lactofermentum* AJ12637 as grown on a nutrient agar medium were inoculated in a sterilized seed medium comprising 2% of sucrose, 0.1% of potassium phosphate, 0.04% of magnesium sulfate, 0.001% of ferrous sulfate, 0.001% of manganese sulfate, 0.4% of ammonium acetate, 0.2% (as total nitrogen) of hydrolysates of soybean protein, 0.04% of L-tyrosine, 100 µg/liter of biotin and 100 µg/liter of vitamin B1, 50 ml of the medium being in a 500 ml-volume shaking flask, and cultured therein by shaking at 31° C. for 24 hours. 10 liters of a fermentation medium comprising 13% of glucose, 1% of ammonium sulfate, 0.15% of potassium phosphate, 0.04% of magnesium sulfate, 0.001% of manganese sulfate, 0.2% (as total nitrogen) of hydrolysates of soybean protein, 0.04% of L-tyrosine, 0.04% of DL-methionine, 1.2% of fumaric acid, 50 µg/liter of biotin and 200 µg/liter of vitamin B1 was put in a 20-liter jar fermenter and sterilized with steam, and the preceding seed culture was added thereto and cultured at a temperature of 31° C. a controlled pH value of 7.0, an air flow rate of 1/3 vvm, an agitation speed of 400 rpm and an inner pressure of 0.1 kg/cm$^2$. Just before glucose in the culture was completely consumed, a sterilized solution containing 60% of glucose was continuously added to the fermenter whereby the glucose concentration in the culture was controlled to be from 1.0 to 2.5%. 55 hours after initiation of the cultivation when the concentration of the accumulated Phe exceeded its solubility, Phe-alpha-crystals in an amount of 1.0% of the concentration of the dissolved Phe were added. The cultivation continued accompanied by precipitation of Phe-alpha-crystals in the culture. In this way, the cultivation was continued for 80 hours to obtain 16 liters of a culture containing 4.8% of Phe (not including the added Phe-alpha-crystals). The thus obtained culture was concentrated and crystallized to separate the crystals, which were then subjected to dissolution and crystallization repeatedly four times. As a result, 0.47 kg of Phe crystals having a purity of 99.5% were obtained. For comparison, cultivation was carried out for 80 hours under the same condition, except that Phe-alpha-crystals were not added during the course of the cultivation. In the comparative case, 15 liters of a culture containing 4.3% of Phe was obtained. This was purified by the same method as above to obtain 0.42 kg of Phe crystals. The results of the two methods are shown in Table 1 below.

TABLE 1

|  | Phe-alpha-crystals added | Conventional method |
| --- | --- | --- |
| Productivity | 0.60 g/liter · hr | 0.54 g/liter · hr |
| Yield | 16% | 15% |

From the results, it is obvious that the continuation of cultivation accompanied with precipitating Phe-alpha-crystals in the culture by addition of seed crystals of Phe-alpha-crystals thereto improved the productivity and yield of Phe.

EXAMPLE 2

Cells of *Bacillus subtilis* AJ12097 as grown on a nutrient agar medium were inoculated in a sterilized seed medium comprising 3% of glucose, 0.1% of ammonium chloride, 0.2% of potassium chloride, 0.1% of potassium phosphate, 0.04% of magnesium sulfate, 0.002% of ferrous sulfate, 0.002% of manganese sulfate, 0.2 (as total nitrogen) of hydrolysates of soybean protein, 0.02% of L-tyrosine and 0.02% of L-tryptophan, 50 ml of the medium being in a 500 ml-volume shaking flask, and cultured therein by shaking at 30° C. for 24 hours. 10 liters of a fermentation medium comprising 13% of glucose, 2% of ammonium chloride, 0.2% of potassium chloride, 0.15% of potassium phosphate, 0.04% of magnesium sulfate, 0.002% of ferrous sulfate, 0.002% of manganese sulfate, 0.2% (as total nitrogen) of hydrolysates of soybean protein, 0.04% of L-tyrosine and 0.04% of L-tryptophan was put in a 20-liter jar fermenter and sterilized with steam, and the preceding seed culture was added thereto and cultured under the same conditions as in Example 1. Just before glucose in the culture was completely consumed, a sterilized solution containing 60% of glucose was continuously added to the fermenter whereby the glucose concentration in the culture was controlled to be from 1.0 to 2.5%. 40 hours after initiation of the cultivation, the controlled pH value of the culture was shifted from 7.0 to 7.8 by introduction of ammonia gas into the culture. The cultivation was continued further accompanied by precipitation of Phe-alpha-crystals in the culture under the shifted condition. As a result of continuation of the cultivation for 100 hours, 16 liters of a culture containing 4.6% of Phe was obtained. This was purified in the same manner as in Example 1 to obtain 0.45 kg of Phe crystals having a purity of 99.5%. For comparison, the cultivation was carried out for 100 hours under the same condition, except that the controlled pH value was not shifted during the course of the cultivation, and 15 liters of a culture containing 4.1% of Phe was obtained. This was purified by the same method as above to obtain 0.4 kg of Phe crystals. The results of the two methods are shown in Table 2 below.

TABLE 2

|  | pH shifted | Conventional method |
|---|---|---|
| Productivity | 0.46 g/liter · hr | 0.41 g/liter · hr |
| Yield | 15% | 14% |

From the results, it is obvious that continuation of the cultivation accompanied by precipitation of Phe-alpha-crystals in the culture by varying the pH value of the culture improved the productivity and yield of Phe.

What is claimed as new and desired to be secured by Letter Patent of the United States is:

1. A method for producing L-phenylalanine comprising:
   i) culturing a bacterium having the ability to produce L-phenylalanine under conditions sufficient to produce L-phenylalanine;
   ii) precipitating α-crystals of L-phenylalanine by adding an effective amount of α-crystals of L-phenylalanine to said culture after the concentration of L-phenylalanine reaches its saturation solubility and before crystals spontaneously precipitate out;
   iii) continuing culturing of said bacterium; and
   iv) isolating said precipitated α-crystals of L-phenylalanine.

2. The method of claim 1, wherein said bacterium is selected from the group consisting of Brevibacterium, Corynebacterium, Bacillus, and Escherichia.

3. The method of claim 1, wherein said bacterium is selected from the group consisting of *Brevibacterium lactofermentum* FERM BP-4160 and *Bacillus subtilis* FERM BP-609.

4. The method of claim 1, wherein said effective amount of α-crystals is 1–5% of the quantity of dissolved L-phenylalanine.

5. A method for producing L-phenylalanine comprising:
   i) culturing a bacterium having the ability to produce L-phenylalanine under conditions sufficient to produce L-phenylalanine;
   ii) precipitating α-crystals of L-phenylalanine by shifting the pH value of said culture to a range of from 7.8 to 8.3 after the concentration of L-phenylalanine reaches its saturation solubility and before crystals spontaneously precipitate out;
   iii) continuing culturing of said bacterium; and
   iv) isolating said precipitated α-crystals of L-phenylalanine.

6. The method of claim 5, wherein said bacterium is selected from the group consisting of Brevibacterium, Corynebacterium, Bacillus, and Escherichia.

7. The method of claim 5, wherein said bacterium is selected from the group consisting of *Brevibacterium lactofermentum* FERM BP-4160 and *Bacillus subtilis* FERM BP-609.

8. The method of claim 5, wherein said pH is shifted by addition of an alkaline substance.

9. The method of claim 8, wherein said alkaline substance is selected from the group consisting of ammonia gas, potassium hydroxide and a mixture thereof.

* * * * *